United States Patent [19]

Amundsen et al.

[11] 4,288,249

[45] Sep. 8, 1981

[54] WATER SOLUBLE PENTACHLOROPHENOL AND TETRACHLOROPHENOL WOOD TREATING SYSTEMS

[75] Inventors: Joseph Amundsen, Federal Way; Robert J. Goodwin, Puyallup; William H. Wetzel, Federal Way, all of Wash.

[73] Assignee: Reichhold Chemicals, Inc., White Plains, N.Y.

[21] Appl. No.: 176,795

[22] Filed: Aug. 11, 1980

Related U.S. Application Data

[63] Continuation of Ser. No. 14,955, Feb. 26, 1979, abandoned, which is a continuation of Ser. No. 857,035, Dec. 2, 1977, abandoned.

[51] Int. Cl.$^3$ ................................................ C09D 5/14
[52] U.S. Cl. ................................. 106/18.35; 424/142; 424/143; 424/347; 427/440
[58] Field of Search .................... 106/18.32, 18.35; 427/440; 424/347, 142, 143

[56] References Cited

U.S. PATENT DOCUMENTS

| | | | |
|---|---|---|---|
| 1,919,298 | 8/1933 | Lehmann et al. | 106/15.05 |
| 2,322,633 | 6/1943 | Hitchens | 424/347 |
| 2,908,607 | 10/1959 | Hager | 424/347 |
| 3,281,318 | 10/1956 | Stutz | 424/347 |
| 3,993,752 | 11/1976 | Stutz | 424/347 |

*Primary Examiner*—Lorenzo B. Hayes
*Attorney, Agent, or Firm*—Munson H. Lane, Jr.; Munson H. Lane

[57] ABSTRACT

This invention relates generally to water soluble wood treating compositions and methods for preservation of wood or products made from wood. In the general practice of this invention, wooden objects are treated with water soluble wood treating and preserving solutions consisting of blends of (A) from 0.1% to about 50% by weight of a chlorophenol selected from a group consisting of pentachlorophenol and tetrachlorophenol and mixtures thereof (B) from about 2% to about 98% by weight aliphatic alcohols selected from the group consisting of n-butyl alcohol, secondary butyl alcohol, isobutyl alcohol, tertiary butyl alcohol and isopropyl alcohol and mixtures thereof (C) from about 0.56% to about 45% of an amine selected from the group consisting of ammonium hydroxide, triethyl amine, trimethyl amine, methyl amine and methyldiethanolamine and mixtures thereof and (D) from about 1% to about 97% by weight water. In addition, these wood treating formulations may contain up to 10% by weight of added ingredients selected from the group of tetrasodium pyrophosphate, copper salts, sodium chromates, sodium gluconate, sodium citrate, sodium n-dihydroxyethyl-glycinate and/or up to 20% by weight ammonium or sodium lignin sulfonate.

4 Claims, No Drawings

WATER SOLUBLE PENTACHLOROPHENOL AND TETRACHLOROPHENOL WOOD TREATING SYSTEMS

This is a continuation, of application Ser. No. 14,955, now abandoned, filed Feb. 26, 1979 which is a continuation of Ser. No. 857,035 filed Dec. 2, 1977 (now abandoned).

BACKGROUND OF THE INVENTION

Wood has been used for many years as an important building and construction material and its importance as such is increasing for a number of reasons. Typical uses include general construction, residential housing, utility poles, cross arms, fence posts, railroad ties and pilings. Although wood is a renewable natural resource, it must be protected from attack by insects and fungus and marine organisms for many of these applications. Left unprotected or unpreserved, wood will decay and deteriorate anywhere from a few months to a few years, depending upon climate and soil conditions. Wood objects such as utility poles and timbers deteriorate rapidly below the ground and at ground level and would require frequent replacement if not properly and adequately preserved with a material which is both effective against attacking organisms and long lasting.

Through the years, a number of different materials have been used for preservation. Among these are included creosote, heavy metal salts, heavy oils and tars, pitch and various organic materials including chlorinated phenols, especially pentachlorophenol (PCP). Each of these materials has its advantages and disadvantages. Creosote, as well as other heavy oils and tars and pitch treatments, may have a strong odor and leave the surface greasy and oily to the touch.

Chlorinated phenols have found wide use because of their effectiveness, relative ease of application and durability. Because of its particularly good fugicidal and insecticidal properties, pentachlorophenol is widely used as a commercial wood preservative. It is normally dissolved in hydrocarbon solvents such as medium aromatic oils, volatile petroleum solvents (propane), light solvents (mineral spirits), or in a chlorinated hydrocarbon solvent-inhibited grade of methylene chloride. Co-solvents are added in many instances to achieve proper solubility of pentachlorophenol in the solutions. Because energy conservation is becoming increasingly important, many of the traditional treating solvents are more valuable as feed stocks for other chemical products. Therefore, a low energy based solvent such as water has been sought as a replacement for these hydrocarbon solvents. The difficulty has been that pentachlorophenol in a simple admixture with water has little or no solubility. Prior art shows that pentachlorophenol can be reacted with sodium hydroxide in water to form the water soluble sodium pentachlorophenate. To date this is the only aqueous soluble form of pentachlorophenol that has been commonly used in the wood treating industry. However, sodium pentachlorophenate treating solution has a severe disadvantage in its excess leachability during field use. In the practice of our invention, new water soluble pentachlorophenol, treating solutions are disclosed which overcome these problems even when using sodium pentachlorophenate.

DETAILED DESCRIPTION OF THE INVENTION

In accordance with this invention, novel pentachlorophenol-aliphatic alcohol-amine or ammonia systems or tetrachlorophenol-aliphatic alcohol-amine or ammonia systems are disclosed that are compatible with water and are soluble therein. Aliphatic alcohols and particularly the butyl alcohols are essential ingredients in solubilizing pentachlorophenol in water even though the butyl alcohols are sparingly water soluble themselves. Volatile amine or ammonia systems are also essential in providing stability and effective penetration of the systems into the wood. Upon contact and penetration into cellulosic materials and during the drying process, the preservative becomes fixed. It has also been found that when soluble metals such as copper sulphate or copper carbonate and chromium salts are included in these treating systems, additional fixation and preservative properties are obtained. In addition, we have found that additives such as tetrasodium pyrophosphate, sodium gluconate, sodium citrate, sodium N-dihydroxyethylglycinate and a lignin sulfonate such as ammonium or sodium lignin sulfonate provide increased effectiveness. In the various formulations, water in widely varying percentages is used as the main solvent.

The pentachlorophenol employed in the present compositions may be present in pure form or as a technical mixture. Pentachlorophenol meeting the requirements of Federal Specification TT-W-570 and American Wood Preservers Association P8-74 is especially suitable. These specifications require that pentachlorophenol contain not less than 95% of chlorinated phenols. It shall contain not more than 1% of matter insoluble in N/1 aqueous sodium hydroxide solution, and it shall have a freezing point of not less than 174° C.

Other chlorinated phenols such as tetrachlorophenol or mixtures of tetra and pentachlorophenol may also be used in place of the pentachlorophenol as well as the sodium salts of these chlorinated phenols.

Several things must be considered when attempting to prepare water soluble pentachlorophenol treating solutions. Acceptable aqueous pentachlorophenol treating solutions must be capable of penetrating deep into the wood and becoming deposited therein in an essentially non-leachable form. Previous attempts to prepare water soluble pentachlorophenol treating solutions could not achieve satisfactory results in either of these two requirements.

Therefore, it was unexpected that water soluble pentachlorophenol treating solutions could be obtained which, in fact, do penetrate deeply into wood and deposit the pentachlorophenol in an essentially non-leachable form in the practice of our invention. These solutions generally comprise pentachlorophenol, a butyl alcohol, an amine or ammonia and water as a solvent. When wood is pressure treated with such a solution and dried, the pentachlorophenol becomes fixed into the wood.

The unexpected discovery of the effectiveness of aliphatic alcohols, especially the butyl alcohols in promoting the solubility of pentachlorophenol into aqueous systems is unique in consideration of the fact that pentachlorophenol itself is very insoluble in water and that n-butyl alcohols are only soluble in water at room temperature to the extent of 9 parts alcohol in 100 parts water.

It was further discovered that the aliphatic alcohol-pentachlorophenol-amine or ammonia water soluble systems could be enhanced by pH control and by additions of further additives.

Mixtures of various alcohols can be used successfully in low amounts in the formulations of our invention as well as the specific alcohols alone. Among the alcohols used alone or in combination as a formulation aid are n-butyl alcohol, isopropyl alcohol, n-propanol, allyl alcohol, secondary butyl alcohol, isobutyl alcohol and tertiary butyl alcohol.

Varying kinds of amines were discovered to be effective in the formulations; preferably the volatile ones. These include various concentrations of ammonia water (ammonium hydroxide) triethyl amine, trimethyl amine, methyl amine, methyldiethanolamine and blends of these amines.

Copper salts which may be used include copper sulfate, copper carbonate, copper hydroxide, copper oxide and copper chloride.

In the practice of our invention, wooden objects are treated with compositions comprising principally blends from about 0.1% to about 50.0% by weight of pentachlorophenol or tetrachlorophenol or mixtures thereof and from about 2.0% to about 98% aliphatic alcohol (particularly n-butyl alcohol) and from about 2.0% to about 45% ammonium hydroxide or amines and from about 1% to about 100% water by weight. In addition, these wood treating formulations may include varying amounts of tetrasodium pyrophosphate (0–10% by weight), copper salts (0–10% by weight), sodium citrate (0–10% by weight, sodium N-dihydroxyethylglycinate (0–10% by weight and a lignin sulfonate such as ammonium or sodium lignin sulfonate (0–20% by weight) as added ingredients.

As stated previously, extreme leachability problems have always been encountered when using water solutions of sodium salts of chlorinated phenols as wood preservatives. By practice of our invention it is now possible to prepare water-borne solutions of sodium pentachlorophenate and tetrachlorophenate which may be deposited in wood in essentially a non-leachable form.

Either pentachlorophenol or tetrachlorophenol may be used and formed into the sodium salt prior to use by reacting with sodium hydroxide or previously prepared commercially available sodium pentachlorophenate or tetrachlorophenate may be used.

If pentachlorophenol or tetrachlorophenol are used as the starting material they are mixed with sodium hydroxide and water. Then the treating solution is prepared from copper sulfate, an amine or ammonia and a lignin sulfonate. In this manner, a treating solution is prepared which, when used to treat the wooden objects of this invention, deposits the chlorophenate in the wood in an essentially non-leachable form. Any of the amine, ammonia or lignin sulfonates previously described may be used. It has been found that solutions may be prepared using from about 0.1% to about 50% by weight pentachlorophenol or tetrachlorophenol, from about 0.02% to about 20% by weight sodium hydroxide; from about 0.5% to about 45% by weight amine or ammonia; from about 0.25% to about 20% by weight lignin sulfonate and from about 0.1% to about 10% by weight copper sulfate. Water may be used from 1% to about 100% by weight.

Various formulations of this invention were prepared and tested as to their effectiveness for wood penetration and wood fixation properties. This involved wood treatment, leaching tests and analysis. The leaching tests and analysis generally conform to American Wood Preserver's association specifications M11-66 Method to Determine Leachability of Wood Preservatives and A5-76 Determination of Chloride for Calculating Pentachlorophenol in Solution or Wood.

The experimental details of leaching tests may be described as follows

Four comparable $\frac{3}{4}'' \times \frac{3}{4}'' \times \frac{3}{4}''$ Douglas fir or Southern pine sapwood blocks treated with like solution retentions were split in two groups. The blocks in Group 1 were directly assayed for pentachlorophenol while the Group 2 blocks were leached and then assayed for pentachlorophenol. The blocks were weighed before and after treatment to determine retentions. Retention of control and leached blocks were considered and corrections made where necessary. The percent pentachlorophenol retained in the leached blocks were reported in the examples by use of the following equation:

$$\frac{\text{leached blocks average PCP assay}}{\text{unleached blocks average PCP assay}} \times 100 = \begin{array}{l}\text{Percent preservative retention}\\ \text{in leached blocks}\end{array}$$

The retained leaching water was also analyzed for preservative content. The treating equipment used for the most part (small scale) was that described in the American Wood Preserver's Association specification M11-66, however, in examples 12 and 13 a larger pilot plant operation was used. This is described in the above noted examples.

In addition, treated wood speciments were given the soil block tests according to AWPA Standard Method M10-63, using Madison 617, Lenzites Trabea and Madison 698 Poria Monticola Murr fungi.

Furthermore, although it was originally intended that the treating compositions of our invention were designed for landsite use, it was discovered that the treated wood would withstand a marine environment as shown in Examples 2 and 10. In these cases leaching with sea water was performed as well as with tap water.

Also, solution stability tests were run to insure that they would not form precipitates under normal treating conditions. Corrosion tests confirmed that the systems are non-corrosive to steel. Bronze or copper should not be used in treating plant equipment where these systems are involved.

A brief explanation of the design of the 42 experimental examples follows

Examples 1 through 13 demonstrate general formulations and testing results of the invention. Examples 17 through 42 serve to demonstrate the wide latitude or ranges of formula ingredients and concentrations that are suitable for obtaining acceptable wood treating solutions. Example 14 serves as a control for the above examples. The formulations in Example 14 do not incorporate the important alcohols of our invention and do not form good solutions since formula solubility is absolutely essential for wood treating purposes.

Although the examples here contain mostly 2% or 3% pentachlorophenol, they can be readily formulated to contain from 1% to 50% pentachlorophenol. The 2% of 3% formulas are used because they more closely conform to the amount generally used in commercially treated wood to meet present military and American Wood Preservers Associations assay retention specifications.

These examples, in general, illustrate the facets and details of this invention, but are not to be construed as limiting the scope to the same.

EXAMPLE 1.

To make 2.5% (by weight) concentration of pentachlorophenol (PCP) treating composition.

FORMULA 2.5 lbs. pentachlorophenol
6.0 lbs. n-butyl alcohol
8.0 lbs. ammonium hydroxide (28%)
83.5 lbs. water The ingredients can be mixed in any order in this and the following experiments, but it is of convenience to dissolve the PCP in n-butyl alcohol (or other alcohols) as solution number 1. Ammonium hydroxide is dissolved in the water as solution number 2. Solutions numbers 1 and 2 are mixed together to provide the final wood treating system. If formulations specify extra ingredients, they can be added next.

The assay results on the borings after treatment of Douglas fir wood are as follows:

| Depth of Penetration | Assay, Lbs. PCP/cu. ft. wood |
|---|---|
| 0.0" to 0.5" zone | 0.68 |
| 0.5" to 1.0" zone | 0.41 |

AWPA leach test results: 79.5% preservative retained using control as 100%.

EXAMPLE 2.

To make 2.0% (by weight) concentration of pentachlorophenol (PCP) in treating composition.

FORMULA 2.0 lbs. pentachlorophenol
6.0 lbs. n-butyl alcohol
8.0 lbs. ammonium hydroxide (28%) 82.56 lbs. water 0.5 lbs. tetrasodium pyrophosphate 0.94 lbs. copper sulfate The assay results on the borings after treatment of Douglas fir wood are as follows:

| Depth of Penetration | Assay, Lbs. PCP/cu. ft. wood |
|---|---|
| 0.0" to 0.5" zone | 0.43 |
| 0.5" to 1.0" zone | 0.38 |

AWPA leach test results: 83.7% preservative retained using control as 100%.
AWPA leach test results (by use of sea water leachant): 80.0% preservative retained using control as 100%.

EXAMPLE 3.

To make 1.7% (by weight) concentration pentachlorophenol (PCP) treating composition.

FORMULA 1.7 lbs. pentachlorophenol
6.0 lbs. n-butyl alcohol
12.0 lbs. ammonium hydroxide (28%)
78.8 lbs. water
0.5 lbs. sodium dichromate
0.5 lbs. copper sulfate
0.5 lbs. tetrasodium pyrophosphate The assay results on the borings after treatment of Douglas Fir wood are as follows:

| Depth of Penetration | Assay, Lbs. PCP/cu. ft. wood |
|---|---|
| 0.0" to 0.5" zone | 0.44 |
| 0.5" to 1.0" zone | 0.30 |

AWPA leach test results: 67.4% preservative retained using control as 100%.

EXAMPLE 4.

To make 2.0% (by weight) concentration of pentachlorophenol (PCP) in treating composition.

FORMULA 2.0 lbs. pentachlorophenol
6.0 lbs. n-butyl alcohol
8.0 lbs. ammonium hydroxide (28%)
82.5 lbs. water
0.5 lbs. sodium gluconate
1.0 lbs. copper sulfate AWPA leach test results: 83.6% preservative retained using control as 100%.

EXAMPLE 5.

To make a 2.0% (by weight) concentration of pentachlorophenol (PCP) in treating composition.

FORMULA 2.0 lbs. pentachlorophenol (PCP)
6.0 lbs. butyl alcohol
8.0 lbs. ammonium hydroxide (28%)
82.7 lbs. water
0.3 lbs. sodium citrate
1.0 lbs. copper sulfate AWPA leach test results: 81.8% preservative retained using control as 100%.

EXAMPLE 6.

To make 3.0% (by weight) concentration of pentachlorophenol (PCP) in treating composition.

FORMULA 3.0 lbs. pentachlorophenol
6.0 lbs. n-butyl alcohol 8.0 lbs. ammonium hydroxide (28%) 81.75 lbs. water 0.25 lbs. sodium N-dihydroxyethylglycinate 1.0 lbs. copper sulfate AWPA leach test results: 98.5% preservative retained using control as 100%.

EXAMPLE 7.

To make 2.0% (by weight) concentration pentachlorophenol (PCP) treating composition.

FORMULA 2.0 lbs pentachlorophenol
6.0 lbs. n-butyl alcohol
8.0 lbs. ammonium hydroxide (28%)
83.2 lbs. water
0.3 lbs. sodium N-dihydroxyethylglycinate
0.5 lbs. copper sulfate AWPA leach test results: 80% preservative retained using control as 100%.

EXAMPLE 8.

To make 1.5% (by weight) concentration pentachlorophenol (PCP) in treating composition.

FORMULA 1.5 lbs. pentachlorophenol
6.0 lbs. n-butyl alcohol
8.0 lbs. ammonium hydroxide (28%)
83.5 lbs. water
0.5 lbs. sodium dichromate
0.5 lbs. copper sulfate AWPA leach test results: 100% preservative retained using control as 100%.

EXAMPLE 9.

To make 2.0% (by weight) concentration pentachlorophenol (PCP) treating composition.

FORMULA 2.0 lbs. pentachlorophenol
6.0 lbs. n-butyl alcohol
8.0 lbs. ammonium hydroxide (28%)
83.0 lbs. water
0.5 lbs. sodium dichromate
0.5 lbs. copper sulfate AWPA leach test results: 100% preservative retained using control as 100%.

EXAMPLE 10.

Two treating compositions containing 2.0% (by weight) concentration of tetrachlorophenol (TCP) were made.

FORMULAE a.
2.0 lbs. tetrachlorophenol
6.0 lbs. butyl alcohol
8.0 lbs. ammonium hydroxide (28%)
82.5 lbs. water
0.5 lbs. tetrasodium pyrophosphate
1.0 lbs. copper sulfate AWPA leach test results: 91% preservative retained using control as 100%.
AWPA leach test results (by use of sea water leachant): 81.9% preservative retained using control as 100%.

b.
2.0 lbs. tetrachlorophenol
6.0 lbs. butyl alcohol
8.0 lbs. ammonium hydroxide (28%)
82.5 lbs. water
0.5 lbs. ammonium lignin sulfonate
1.0 lbs. copper sulfate AWPA leach test results: 83% perservative retained using control as 100%.
AWPA leach test results (by use of sea water leachant): 80% preservative retained using control as 100%.

EXAMPLE 11.

To make 2% (by weight) concentration of tetrachlorophenol (PCP) treating composition.

FORMULA 2.0 lbs. tetrachlorophenol
6.0 lbs. n-butyl alcohol
10.0 lbs. ammonium hydroxide (23%)
0.5 lbs. ammonium lignin sulfonate
1.0 lbs. copper sulfate
80.5 lbs. water The assay results on the borings after treatment of the Douglas Fir wood are as follows:

| Depth of Penetration | Assay, lbs. PCP/cu. ft. wood |
| --- | --- |
| 0.0" to 0.5" zone | 0.58 |
| 0.5" to 1.0" zone | 0.66 |

EXAMPLE 12.

To make 2.0% (by weight) concentration of pentachlorophenol (PCP) in treating composition.

FORMULA 2.0 lbs. pentachlorophenol
0.5 lbs. sodium hydroxide
8.0 lbs. ammonium hydroxide (24%)
85.5 lbs. water
3.0 lbs. ammonium lignin sulfonate (51%)
1.0 lbs. copper sulfate

TEST CONDITIONS

The experiment using the above composition was conducted in a large scale experimental retort $7\frac{1}{2}$ feet in length by 15 inches in diameter. The initial vacuum was 28 inches Hg for one half hour, then 135 lbs. pressure was applied to the treating load for 18 hours. The treated posts were 6 feet, 6 inches long by 6–7 inches in diameter.

RESULTS ON SOUTHERN PINE POST TREATMENT

The assay results on the borings taken from the treated wood are as follows:

| Depth of Penetration | Assay, lbs. PCP/cu. ft. wood |
| --- | --- |
| 0.0" to 0.5" zone | 1.06 |
| 0.5" to 1.0" zone | 0.69 |
| 1.0" to 1.5" zone | 0.69 |
| 1.5" to 2.0" zone | 0.71 |

EXAMPLE 13.

To make 2.0% (by weight) concentration of tetrachlorophenol (TCP) in treating composition.

FORMULA 2.0 lbs. tetrachlorophenol
0.5 lbs. sodium hydroxide
7.0 lbs. ammonium hydroxide (24%)
86.5 lbs. water
3.0 lbs. ammonium lignin sulfonate (51%)
1.0 lbs. copper sulfate

TEST CONDITIONS

The experiment using the above composition was conducted in a large scale experimental retort $7\frac{1}{2}$ feet in length by 15 inches in diameter. The initial vacuum was 28 inches Hg for one half hour, then 135 lbs. pressure was applied to the treating load for 18 hours. The treated posts were 6 ft. 6 inches long by 6–7 inches in diameter.

RESULTS ON THE WOOD POST TREATMENT

The assay results on the borings taken from the treated Southern pine wood are as follows:

| Depth of Penetration | Assay, lbs. TCP/cu. ft. wood |
|---|---|
| 0.0" to 0.5" zone | 0.83 |
| 0.5" to 1.0" zone | 0.57 |
| 1.0" to 1.5" zone | 0.51 |
| 1.5" to 2.0" zone | 0.47 |

The assay results on the borings taken from the treated Douglas fir wood are as follows:

| Depth of Penetration | Assay, lbs. TCP/cu. ft. wood |
|---|---|
| 0.0" to 0.5" zone | 0.67 |
| 0.5" to 1.0" zone | 0.40 |

EXAMPLE 14.

To make 2-2.5 (by weight) concentration of pentachlorophenol, in absence of n-butyl alcohol or other alcohols, the following formulas were attempted:

FORMULAE a.
2.0 lbs. pentachlorophenol
8.0 lbs. ammonium hydroxide (28%)
90.0 lbs. water b.
2.5 lbs. pentachlorophenol
25.0 lbs. ammonium hydroxide (28%)
72.5 lbs. water c.
2.5 lbs. pentachlorophenol
25.0 lbs. ammonium hydroxide (28%)
71.0 lbs. water
1.0 lbs. copper sulfate
0.5 lbs. tetrasodium pyrophosphate These formulations formed insoluble mixtures and thus were not suitable for wood treatments in the absence of butyl alcohol.

EXAMPLE 15.

To make 3.0% (by weight) concentration of sodium pentachlorophenol in treating composition.

FORMULA 3.0 lbs. sodium pentachlorophenate
4.0 lbs. n-butyl alcohol
93.0 lbs. water The assay results on the borings after treatment of the Douglas Fir wood are as follows:

| Depth of Penetration | Assay, lbs. PCP/cu. ft. wood |
|---|---|
| 0.0" to 0.5" zone | 0.90 |
| 0.5" to 1.0" zone | 0.75 |

AWPA leach test results: 20.8% preservative retained using control as 100%.

EXAMPLE 16.

A 3.0% (by weight) concentration of sodium pentachlorophenate in treating composition was made in the absence of butyl alcohol.

FORMULA 3.0 lbs. sodium pentachlorophenate
97.0 lbs. water

The assay results on the borings after treatment of Douglas Fir wood are as follows:

| Depth of Penetration | Assay, lbs. PCP/cu. ft. wood |
|---|---|
| 0.0" to 0.5" zone | 1.1 |
| 0.5" to 1.0" zone | 0.04 |

EXAMPLE 17.

To make 2.5% (by weight) concentration of pentachlorophenol (PCP) treating composition.

FORMULA 2.5 lbs. pentachlorophenol
8.0 lbs. n-propanol
8.0 lbs. ammonium hydroxide (28%)
81.5 lbs. water

EXAMPLE 18.

To make 2.5% (by weight) concentration of pentachlorophenol (PCP) in treating composition.

FORMULA 2.5 lbs. pentachlorophenol
10.0 lbs. allyl alcohol
8.0 lbs. ammonium hydroxide (28%)
79.5 lbs. water

EXAMPLE 19.

To make 2.5% (by weight) concentration of pentachlorophenol (PCP) in treating composition.

FORMULA 2.5 lbs. pentachlorophenol
6.0 lbs. secondary butyl alcohol
8.0 lbs. ammonium hydroxide (28%)
83.5 lbs. water

EXAMPLE 20.

To make 2.5% (by weight) concentration of pentachlorophenol (PCP) in treating composition.

FORMULA 2.5 lbs. pentachlorophenol
6.0 lbs. iso-butyl alcohol
8.0 lbs. ammonium hydroxide (28%)
83.5 lbs. water

EXAMPLE 21.

To make 2.5% (by weight) concentration of pentachlorophenol (PCP) in treating composition.

FORMULA 2.5 lbs. pentachlorophenol
10.0 lbs. tertiary butyl alcohol
8.0 lbs. ammonium hydroxide (28%)
79.5 lbs. water

EXAMPLE 22.

To make 1.0% (by weight) concentration of pentachlorophenol (PCP) in treating composition.
1.0 lbs. pentachlorophenol
2.0 lbs. n-butyl alcohol
3.0 lbs. ammonium hydroxide (28%)
94.0 lbs. water

EXAMPLE 23.

To make 0.1% (by weight) concentration of pentachlorophenol (PCP) in a treating composition.

FORMULA 0.1 lbs. pentachlorophenol
2.0 lbs. n-butyl alcohol
2.0 lbs. ammonium hydroxide (28%)
95.9 lbs. water

EXAMPLE 24.

To make 10.0% (by weight) concentration of pentachlorophenol (PCP) in a treating composition.

FORMULA 10.0 lbs. pentachlorophenol
12.0 lbs. n-butyl alcohol
12.0 lbs. ammonium hydroxide (28%)
66.0 lbs. water

EXAMPLE 25.

To make 1.0% (by weight) concentration of pentachlorophenol (PCP) in a treating composition.

FORMULA 1.0 lbs. pentachlorophenol
97.0 lbs. n-butyl alcohol
2.0 lbs. ammonium hydroxide (28%)

EXAMPLE 26.

To make 50.0% (by weight) concentration of pentachlorophenol (PCP) in a treating composition.

FORMULA 50.0 lbs. pentachlorophenol
48.0 lbs. n-butyl alcohol
2.0 lbs. ammonium hydroxide (28%)

EXAMPLE 27.

To make 25.0% (by weight) concentration of pentachlorophenol (PCP) in a treating composition.

FORMULA 25.0 lbs. pentachlorophenol
30.0 lbs. n-butyl alcohol
45.0 lbs. ammonium hydroxide (28%)

EXAMPLE 28.

To make 2.0% (by weight) concentration of pentachlorophenol (PCP) treating composition.

FORMULA 2.0 lbs. pentachlorophenol
6.0 lbs. n-butyl alcohol
8.0 lbs. ammonium hydroxide (28%)
1.0 lbs. copper sulfate
10.0 lbs. sodium N-dihydroxyethylglycinate
73.0 lbs. water

EXAMPLE 29.

To make 2.5% (by weight) concentration of pentachlorophenol (PCP) treating composition.

FORMULA 2.5 lbs. pentachlorophenol
6.0 lbs. n-butyl alcohol
15.0 lbs. ammonium hydroxide (14%)
76.5 lbs. water

EXAMPLE 30.

To make 2.0% (by weight) concentration of pentachlorophenol (PCP) treating composition.

FORMULA 2.0 lbs. pentachlorophenol
4.0 lbs. n-butyl alcohol
4.0 lbs. isopropyl alcohol
80.5 lbs. water
8.0 lbs. ammonium hydroxide (28%)
0.5 lbs. tetrasodium pyrophosphate
1.0 lbs. copper sulfate

EXAMPLE 31.

To make 3.0% (by weight) concentration of pentachlorophenol (PCP) treating composition.

FORMULA 3.0 lbs. pentachlorophenol
4.0 lbs. n-butyl alcohol
4.0 lbs. isopropyl alcohol
81.0 lbs. water
8.0 lbs. ammonium hydroxide (28%)

EXAMPLE 32.

To make 2.0% (by weight) concentration of pentachlorophenol (PCP) in a treating composition.

FORMULA 2.0 lbs. pentachlorophenol
4.0 lbs. n-butyl alcohol
4.0 lbs. isopropyl alcohol
80.5 lbs. water
8.0 lbs. ammonium hydroxide (28%)
0.5 lbs. tetrasodium pyrophosphate
1.0 lbs. copper sulfate

EXAMPLE 33.

To make 2.0% (by weight) concentration of pentachlorophenol (PCP) in a treating composition.

FORMULA 2.0 lbs. pentachlorophenol
6.0 lbs. butyl alcohol
3.0 lbs. triethyl amine
85.5 lbs. water
0.5 lbs. tetrasodium pyrophosphate
3.0 lbs. acetone

EXAMPLE 34.

To make 2.0% (by weight) concentration of pentachlorophenol (PCP) is a treating composition.

FORMULA 2.0 lbs. pentachlorophenol
6.0 lbs. butyl alcohol
3.0 lbs. trimethyl amine

EXAMPLE 35.

To make 2.0% (by weight) concentration of pentachlorophenol (PCP) in a treating composition.

FORMULA 2.0 lbs. pentachlorophenol
6.0 lbs. butyl alcohol
3.0 lbs. methyldiethanolamine
89.0 lbs. water

EXAMPLE 36.

To make 2.0% (by weight) concentration of pentachlorophenol (PCP) in a treating composition.

FORMULA 2.0 lbs. pentachlorophenol
6.0 lbs. n-butyl alcohol
89.0 lbs. water
3.0 lbs. methyl amine

EXAMPLE 37.

To make 2.0% (by weight) concentration of pentachlorophenol (PCP) treating composition

FORMULA 2.0 lbs. pentachlorophenol
6.0 lbs. n-butyl alcohol
8.0 lbs. ammonium hydroxide (28%)
82.0 lbs. water
1.0 lbs. ammonium lignin sulfonate
1.0 lbs. copper sulfate

EXAMPLE 38.

To make 2.0% (by weight) concentration of tetrachlorophenol-pentachlorophenol treating composition.

FORMULA 1.0 lbs. pentachlorophenol
1.0 lbs. tetrachlorophenol
6.0 lbs. n-butyl alcohol
8.0 lbs. ammonium hydroxide (28%)
82.5 lbs. water
0.5 lbs. ammonium lignin sulfate
1.0 lbs. ammonium sulfate
1.0 lbs. copper sulfate

EXAMPLE 39.

To make 2.0% (by weight) concentration of pentachlorophenol (PCP) treating composition.

FORMULA 2.0 lbs. pentachlorophenol
6.0 lbs. n-butyl alcohol
8.0 lbs. ammonium hydroxide (28%)
82.0 lbs. water
1.0 lbs. sodium lignin sulfonate
1.0 lbs. copper sulfate

EXAMPLE 40.

To make 2% (by weight) concentration of sodium pentachlorophenate treating solution using sodium pentachlorophenate.

FORMULA 12.0 lbs. sodium pentachlorophenate (16.7% concentrate)
74.0 lbs. water
10.0 lbs. ammonium hydroxide
3.0 lbs. ammonium lignin sulfonate
1.0 lbs. copper sulfate

EXAMPLE 41.

To make a 2% (by weight) concentration of sodium pentachlorophenate treating solution using pentachlorophenol.

FORMULA 2.0 lbs. pentachlorophenol
0.75 lbs. sodium hyroxide
83.25 lbs. water
10.0 lbs. ammonium hydroxide
3.0 lbs. ammonium lignin sulfonate
1.0 lbs. copper sulfate

EXAMPLE 42.

To make a 2% (by weight) concentration of sodium tetrachlorophenate treating solution using tetrachlorophenol 2.0 lbs. tetrachlorophenol
0.6 lbs. sodium hydroxide
83.4 lbs. water
10.0 lbs. ammonium hydroxide
3.0 lbs. ammonium lignin sulfonate
1.0 lbs. copper sulfate

What is claimed is:

1. Water soluble wood treating and preserving solutions consisting of blends of (A) from about 0.1% to about 50% by weight of a chlorophenol selected from a group consisting of pentachlorophenol and tetrachlorophenol and mixtures thereof (B) from about 2% to about 98% by weight aliphatic alcohols selected from the group consisting of N-butyl alcohol, secondary butyl alcohol, isobutyl alcohol, tertiary butyl alcohol and isopropyl alcohol and mixtures thereof (C) from about 0.56% to about 45% by weight of an amine selected from the group consisting of ammonium hydroxide, triethylamine, trimethyl amine, methyl amine and methyldiethanol amine and mixtures thereof and (D) from about 1% to about 97% by weight water.

2. The water soluble wood treating and preserving solutions according to claim 1 further containing at least one member selected from the group consisting of: tetrasodium pyrophosphate, copper salts, sodium citrate, sodium n-dihydroxyethylglycinate, ammonium lignin sulfonate and sodium lignin sulfonate.

3. Water soluble wood treating and preserving solutions consisting of blends of (A) from about 0.1% to about 50% by weight of a chlorophenol selected from a group consisting of pentachlorophenol and tetrachlorophenol and mixtures thereof (B) from about 2% to about 98% by weight aliphatic alcohols selected from the group consisting of N-butyl alcohol, secondary butyl alcohol, isobutyl alcohol, tertiary butyl alcohol and isopropyl alcohol and mixtures thereof (C) from about 0.56% to about 45% by weight of an amine selected from the group consisting of ammonium hydroxide, triethyl amine, trimethyl amine, methyl amine and methyldiethanol amine and mixtures thereof (D) from about 1% to about 97% by weight water and (E) and from 0.02% to about 20% by weight sodium hydroxide.

4. The water soluble wood treating and preserving solutions according to claim 3 further containing at least one member selected from the group consisting of: tetrasodium pyrophosphate, copper salts, sodium citrate, sodium n-dihydroxyethylglycinate, ammonium lignin sulfonate and sodium lignin sulfonate.

* * * * *